United States Patent
Lorenzini et al.

(10) Patent No.: US 9,974,568 B2
(45) Date of Patent: May 22, 2018

(54) ARTICULATED DEVICE FOR THE WRIST

(71) Applicant: ORTHOFIX S.R.L., Verona (IT)

(72) Inventors: Denis Lorenzini, Verona (IT); Andrea Ottoboni, Rovigo (IT)

(73) Assignee: Orthofix S.R.L., Verona (IT)

( * ) Notice: Subject to any disclaimer, the term of this patent is extended or adjusted under 35 U.S.C. 154(b) by 294 days.

(21) Appl. No.: 14/778,069

(22) PCT Filed: Mar. 11, 2014

(86) PCT No.: PCT/EP2014/000645
§ 371 (c)(1),
(2) Date: Sep. 17, 2015

(87) PCT Pub. No.: WO2014/146766
PCT Pub. Date: Sep. 25, 2014

(65) Prior Publication Data
US 2016/0287289 A1    Oct. 6, 2016

(30) Foreign Application Priority Data
Mar. 18, 2013   (IT) .............................. MI2013A0409

(51) Int. Cl.
*A61B 17/64*   (2006.01)
*A61B 17/66*   (2006.01)

(52) U.S. Cl.
CPC .......... *A61B 17/6425* (2013.01); *A61B 17/66* (2013.01)

(58) Field of Classification Search
CPC ...... A61B 17/64; A61B 17/66; A61B 17/6425
See application file for complete search history.

(56) References Cited

U.S. PATENT DOCUMENTS 5,437,667 A * 8/1995 Papierski ........... A61B 17/6425
606/55
5,662,649 A    9/1997 Huebner
(Continued)

FOREIGN PATENT DOCUMENTS

WO      94/10947 A1    5/1994
WO   2011/049471 A1    4/2011

OTHER PUBLICATIONS

International Search Report, PCT/EP2014/000645, dated Jun. 10, 2014, 4 pages.
(Continued)

*Primary Examiner* — Christopher Beccia
(74) *Attorney, Agent, or Firm* — Baker & McKenzie LLP

(57) ABSTRACT

Articulated device (1) for the wrist comprising: a proximal connector (2) for housing a proximal attachment system for pins; —a distal connector (3) for housing a distal attachment system for pins; an articulator joint (4) to provide a controlled movement between the proximal connector (2) and the distal connector (3), characterized in that said articulator joint (3) comprises an arched element (5) that is rotatably mounted on a support element (6) in order to enable rotation around an axis of rotation (X) corresponding to the axis of rotation by flexion and extension of the wrist, said arched element (5) being directly connected to the distal connector (3), blocking means (51) to block the rotation of the arched element (5) and rotation-limiting means (53) to limit the rotation of the arched element (5) for a pre-established portion of a circumferential arc are both directly mounted on said support element (6), and in that said support element (6) is mounted by means of a simple cardan joint (40) on the proximal connector (2), said simple cardan joint (40) presenting a first axis of rotation (Z) that is perpendicular to the axis of rotation (X) of the arched element and a second axis of rotation (Y) that is perpendicular to the first axis of (Continued)

rotation (Z) and movable with respect to the axis of rotation (X) of the arched element along a circumferential arc whose center is located on the first axis of rotation (Z).

12 Claims, 5 Drawing Sheets

(56) References Cited

U.S. PATENT DOCUMENTS

| | | | |
|---|---|---|---|
| 6,428,540 B1 * | 8/2002 | Claes | A61B 17/66 606/53 |
| 2008/0275555 A1 | 11/2008 | Makower et al. | |
| 2011/0087297 A1 | 4/2011 | Orbay et al. | |
| 2012/0296434 A1 | 11/2012 | Kumar | |

OTHER PUBLICATIONS

Written Opinion of the International Searching Authority, PCT/EP2014/000645, dated Jun. 10, 2014, 5 pages.

* cited by examiner

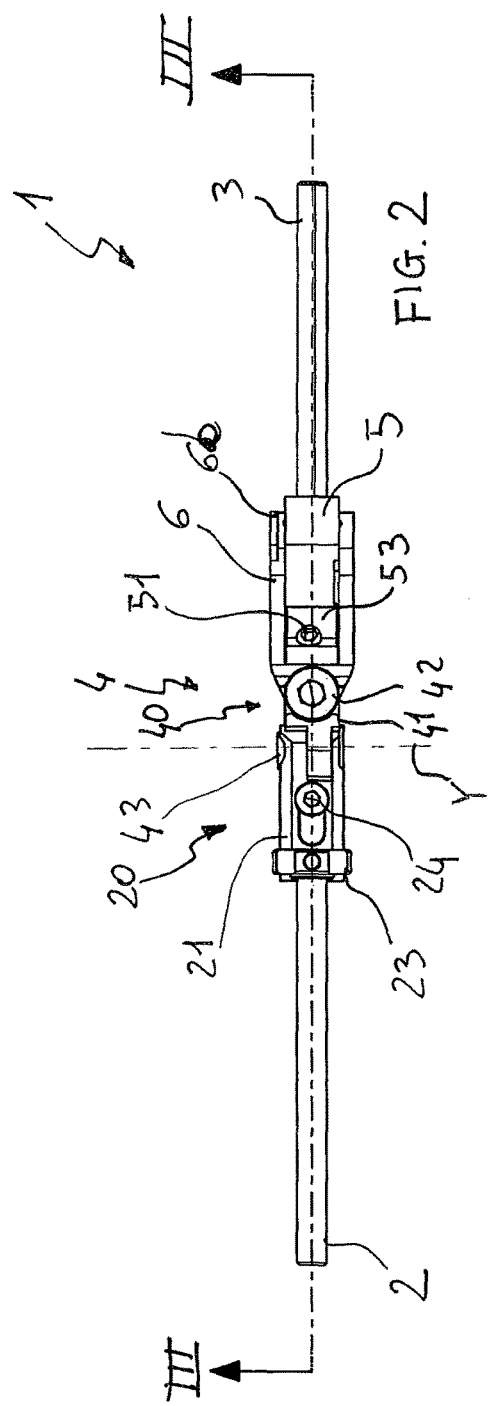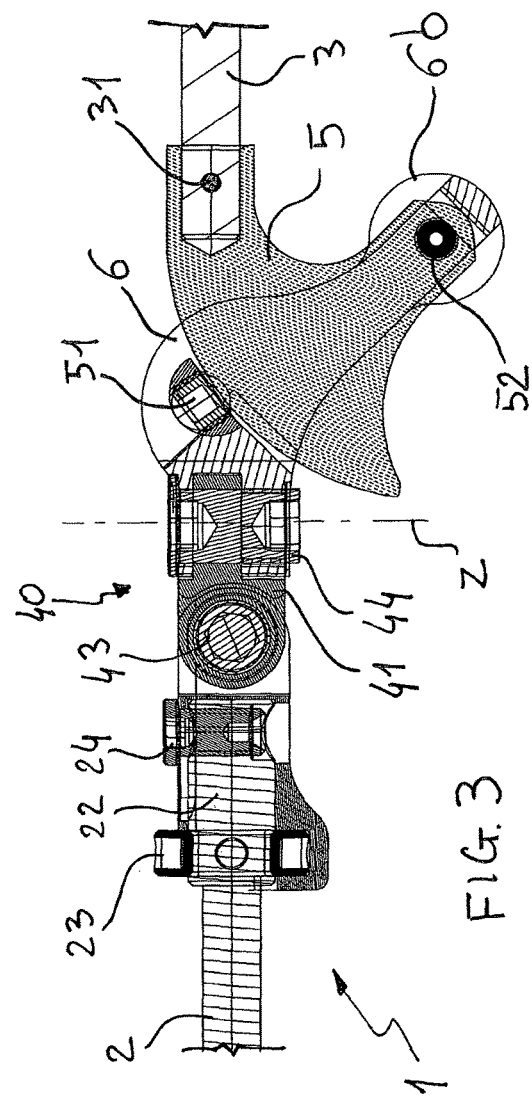

ARTICULATED DEVICE FOR THE WRIST

FIELD OF APPLICATION

The present invention applies to the field of articulated devices used for the treatment of fractures in the wrist region.

PRIOR ART

For wrist fractures the treatment can be bloodless (reduction and constriction in a brachio-metacarpal or antibrachio-metacarpal plaster device for 5-6 weeks) or surgical, which is nowadays resorted to more often than in the past, of osteosynthesis with external fixation systems in radius distal metaepiphyseal fractures or with plate and pins.

Referring to external fixators, they can be divided, according to the type of functions the fixator is able to perform during or after its application to a patient, into: real stabilizers or articulated devices.

Stabilizers are characterized in that they allow a group of proximal pins to be connected to a group of distal pins, these pins can be directly applied onto a rod or into a clamp. These stabilization devices require a correct fracture reduction before tightening clamps.

Articulated devices can be of the type allowing compression and distraction in the fracture site to be performed after being suitably attached to the limbs by means of groups of proximal and distal pins or of the type allowing, besides enabling a compression/distraction to be performed, also the joint to be moved after attaching the device to the limbs.

In particular, the above-mentioned articulator devices of the last type quite generally comprise a proximal attachment system for the pins, a distal attachment system for the pins and an articulator joint, which is connected to the respective proximal and distal systems by means of suitable connection devices.

Some articulator devices belonging to this last category are known, intended to allow the hand to move with respect to the wrist during the recovery step.

In order to better repeat the natural movements of the wrist joint, some devices have been developed, that are extremely complex from the structural point of view, with large overall dimensions, complicated to apply for the doctor and uncomfortable to use for the patient as well.

The devices that on the contrary have not at least one of these drawbacks are distinguishable by their limited effectiveness in reproducing at best the joint movement.

The technical problem underlying the present invention is therefore to provide an articulated device for the wrist allowing the patient wearing it to move the hand in a natural way with respect to the wrist without compromising the recovery, within a simple, extremely compact and easy-to-use structural solution.

Moreover, the articulated device for the wrist according to the present invention allows the wrist to be kept in a fixed position with respect to bones when that use is required.

In addition, the articulated device for the wrist according to the present invention allows both a compression-extension movement and an abduction-adduction movement or selectively only one thereof to be performed.

SUMMARY OF THE INVENTION

Said technical problem is solved by an articulated device for the wrist according to claim 1.

Further features and advantages will become more apparent from the following detailed description of some preferred, but not exclusive, embodiments of the present invention, with reference to the attached figures, given by way of non-limiting examples.

BRIEF DESCRIPTION OF THE DRAWINGS

FIG. 2 is a view from above of the device of FIG. 1;

FIG. 3 is a sectional view taken along the line of FIG. 2;

DETAILED DESCRIPTION

Figure 1:
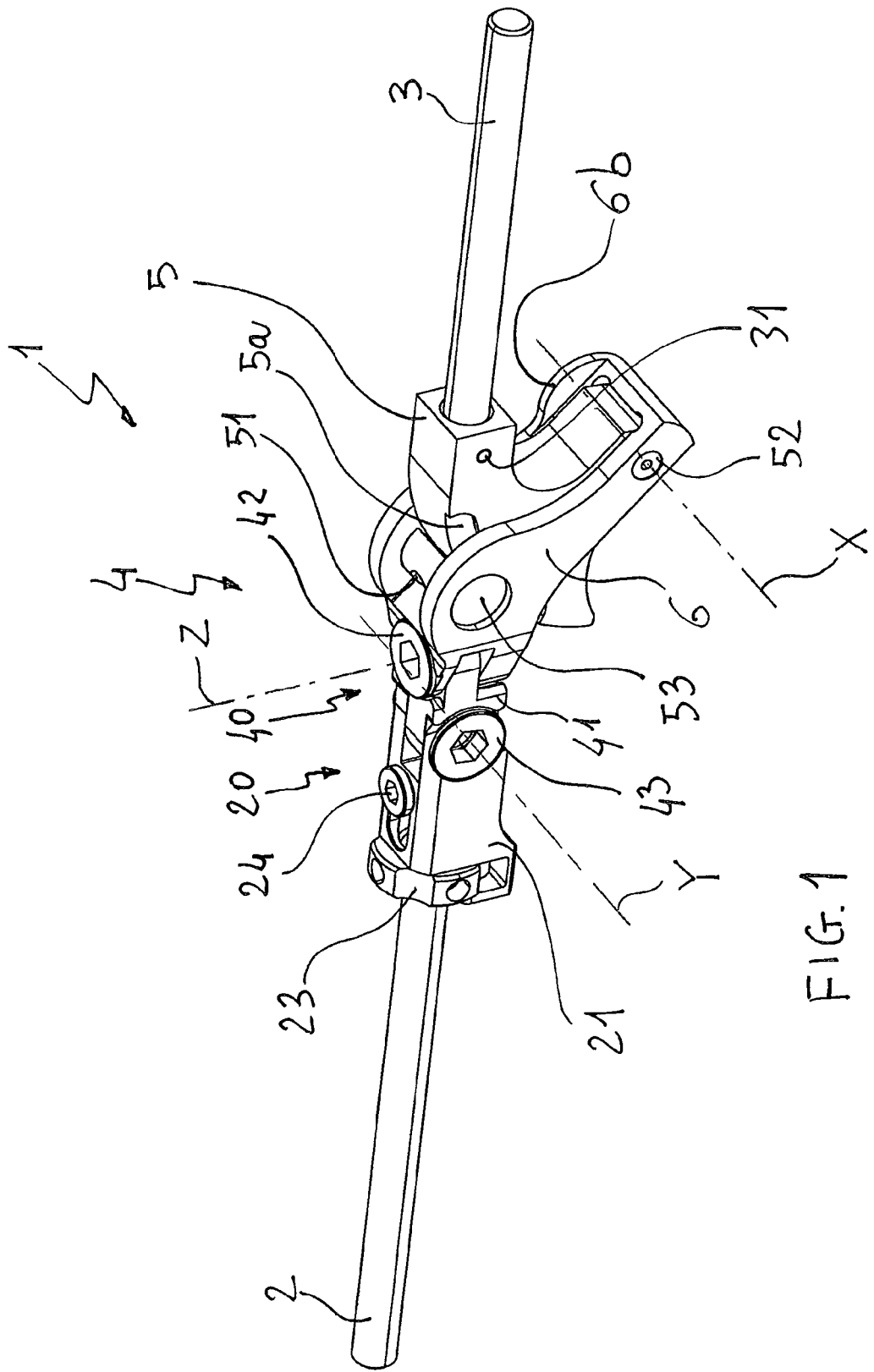
FIG. 1 is a perspective view of the articulated device for the wrist according to the present invention.

Referring to the attached figures, and particularly to FIGS. 1-5, an articulated device for the wrist according to the present invention has been indicated with reference number 1.

The articulated device 1 for the wrist comprising, more generally:
a proximal connector 2 for housing a proximal attachment system for pins that are inserted in a proximal bone of the fracture,
a distal connector 3 for housing a distal attachment system for pins that are inserted in a distal bone of the fracture;
an articulator joint 4 to provide a controlled movement between the proximal connector 2 and the distal connector 3.

In the example shown the proximal connector 2 and the distal connector 3 actualize in a proximal rod and in a distal rod respectively that the clamps supporting the pins can be attached to, the latter ones, in case of fracture in the wrist region, such as for example distal radius fractures, are attached to the radius and to metacarpal bones respectively.

Figure 4:
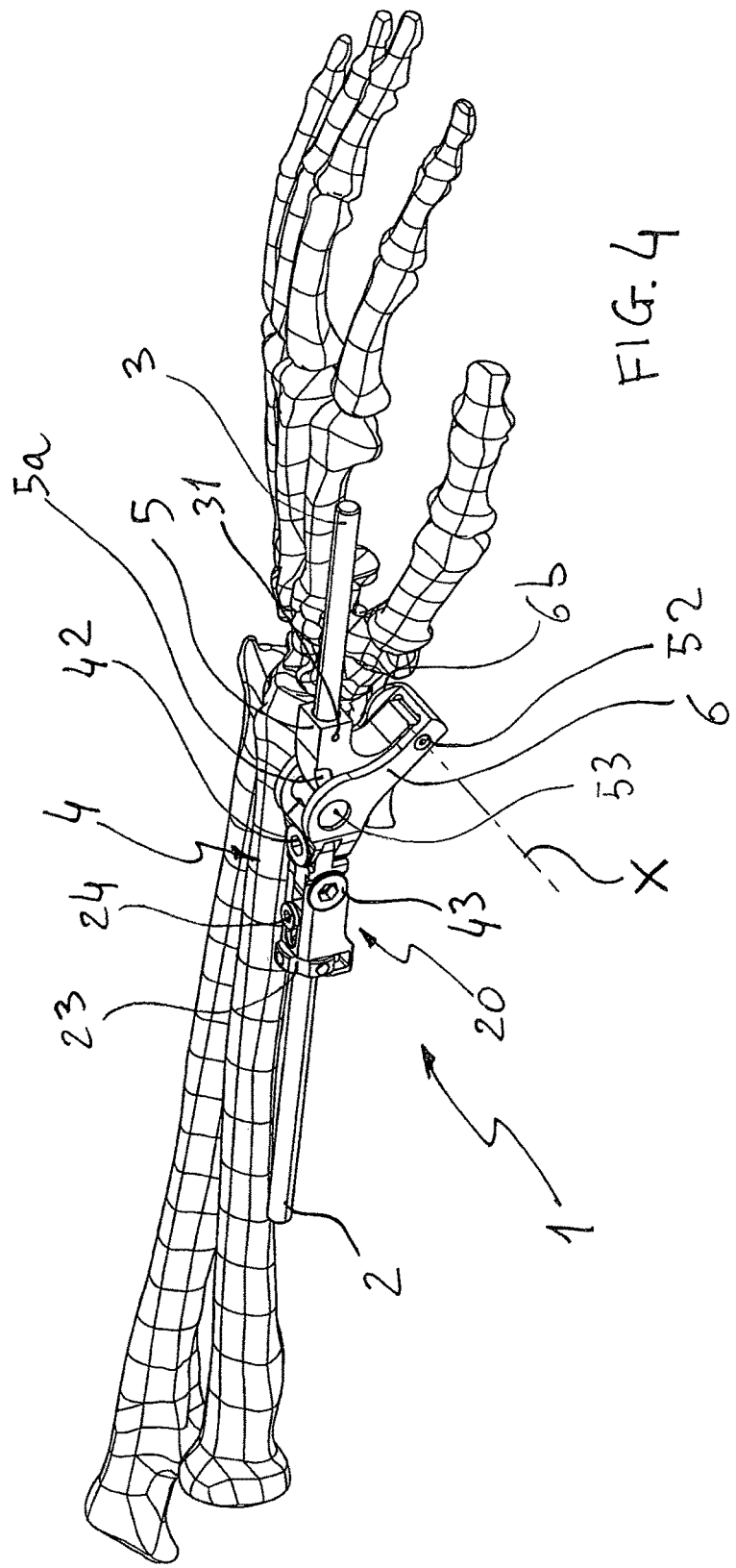
FIG. 4 shows the arrangement in space of the device with respect to the wrist region.
Figure 5:
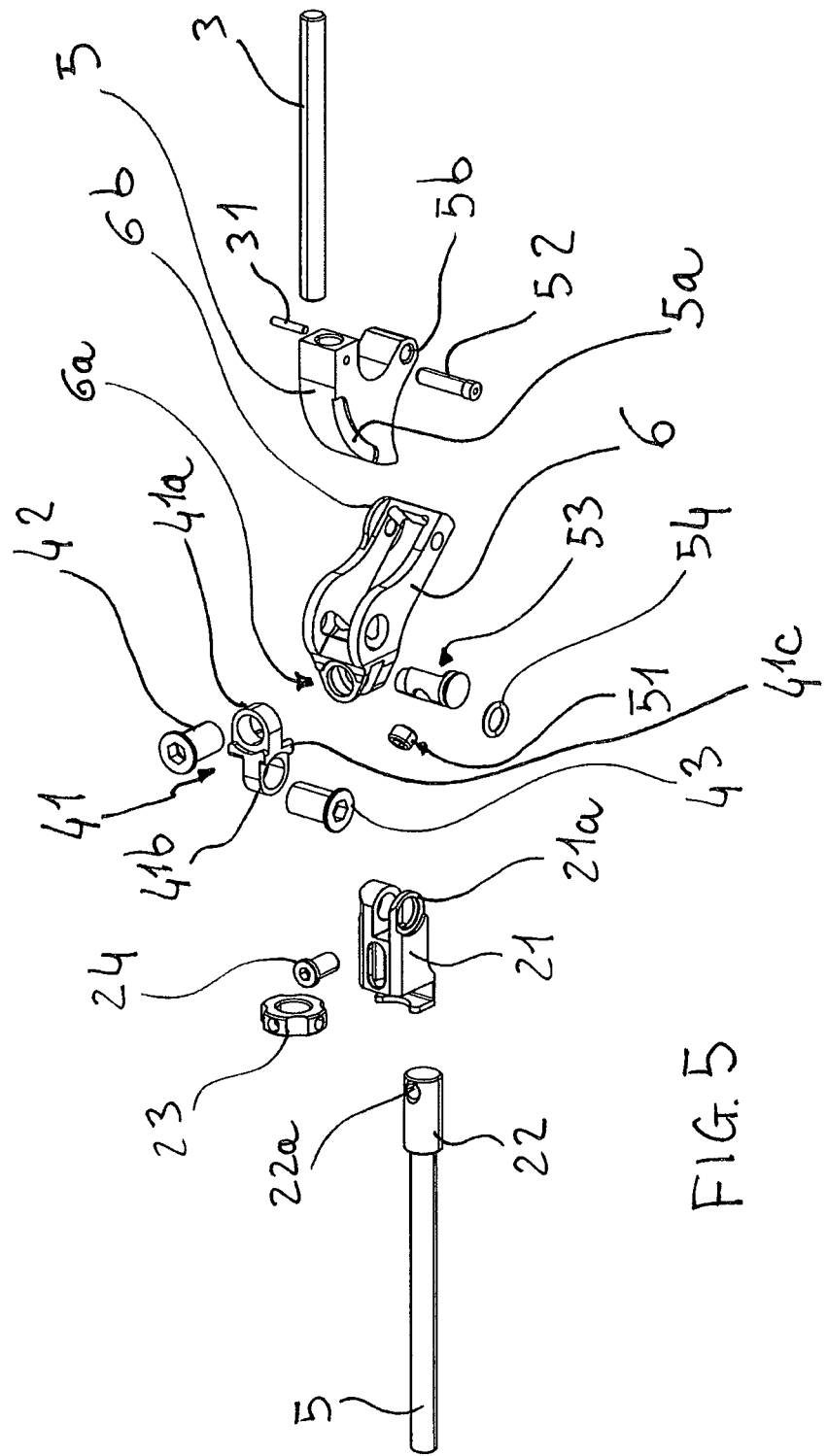
FIG. 5 is an exploded view of the device of FIG. 1.
Figure 6:
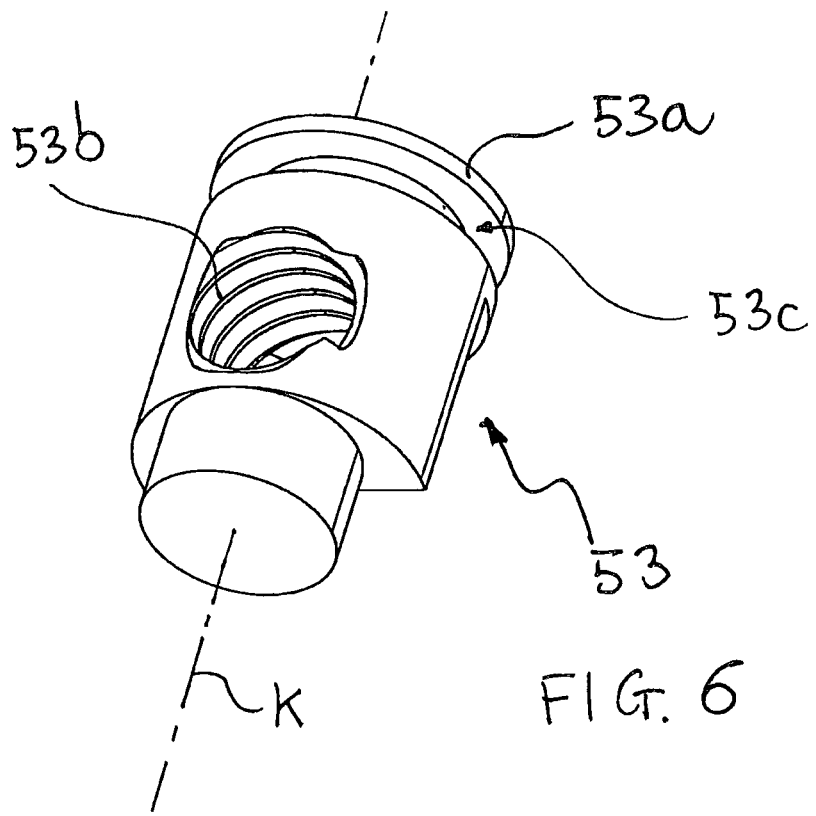
FIGS. 6 and 7 show different views of an insert for limiting the rotation of the arched element.
Figure 7:
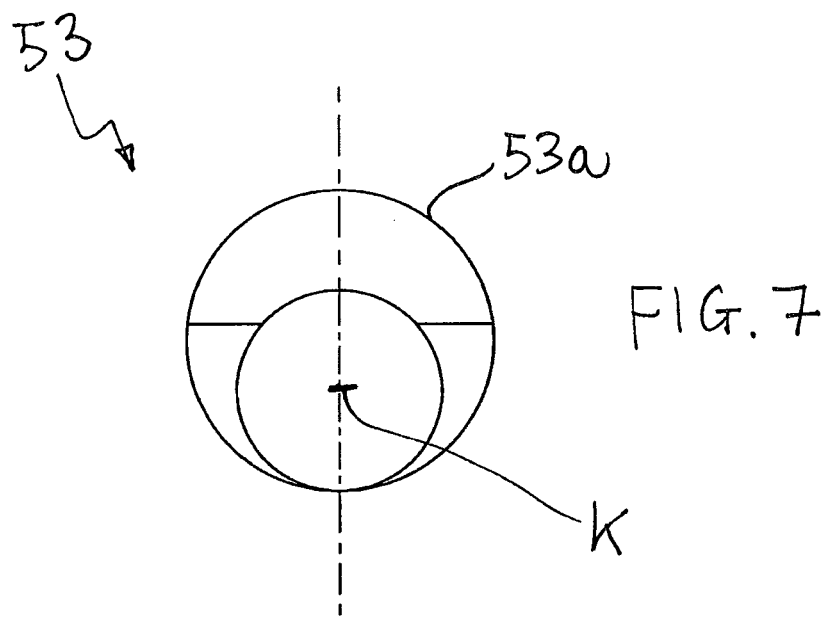

According to the present invention, the articulator joint 4 comprises an arched element 5 that is rotatably mounted on a support element 6 in order to enable rotation around an axis of rotation X located in correspondence with the instant center of rotation of the wrist (as it can be seen in FIG. 4). The arched element 5 is connected, at an end thereof, to the distal rod 3 by means of a peg 31 that is inserted into a corresponding seat that is present in the arched element 5.

Suitable blocking means for blocking the rotation of the arched element 5 and rotation-limiting means for limiting the rotation of the arched element 5 for a pre-established portion of a circumferential arc are both directly mounted on the support element 6. These blocking means and limiting means will be better described hereafter.

According to the invention, the support element 6 is mounted by means of a simple cardan joint 40 on the proximal connector 2, this simple cardan joint 40 has a first axis of rotation Z that is perpendicular to the axis of rotation X of the arched element 5 and a second axis of rotation Y that is perpendicular to the first axis of rotation Z, this latter axis Z is movable with respect to the axis of rotation of the arched element X along a circumferential arc whose center is located on the first axis of rotation Z.

The articulated device 1 can act as an external fixator having the various elements composing it blocked together.

In the example shown, the arched element 5 has a hole 5b passed through by a pin 52 which it is hinged on. The pin 52 has a hole in its center to allow a Kirchner wire to pass through, that hole has a central axis coinciding with the axis of rotation X.

In practice, the center of rotation of the arched element 5 coincides with the center of rotation of the wrist, in order to obtain a perfect centering of the articulated device 1.

In the preferred embodiment of the present invention, the blocking means of the rotation of the arched element 5 comprise a locking grub screw 51 that can be operated in rotation from the outside, whose end is intended to abut against an edge of the arched element 5. The limiting means comprise on the contrary an axially displaceable insert 53. In the example, the insert 53 is provided with a threaded channel 53*b* which the blocking grub screw 51 screws into.

The blocking grub screw 51 is provided on the head with a shaped impression, preferably hexagon-like, for engaging with a screwing tool.

The insert 53 has a cylindrical shape, whose threaded channel 53*b* which the blocking grub screw 51 passes through extends transversely, moreover it has an eccentric body 53*a* at an end thereof that is intended to abut against a ribbed profile 5*a* that is present on a perimeter portion of the arched element 5.

The insert 53 is axially movable along an axis K between a position wherein the eccentric body 53*a* is inserted into the rib 5*a* of the arched element 5 therefore limiting the angular travel of the arched element to about 45°. When on the contrary the insert 53 is operated in order to move the eccentric body 53*a* away till going out of the rib 5*a*, the arched element 5 is free to rotate along a circumferential arc of about 60°-80°.

The operation along the axis K of the insert 53 can occur also tangentially moving the grub screw 51 inserted into the insert 53.

A friction ring 54 is located within an annular rib 53*c* that is present in correspondence with the eccentric body 53*a*.

The simple cardan joint 40 comprises a connecting element 41 formed by a pair of annular elements 41*a*, 41*b* having the respective central axis corresponding to the first and second axis of rotation Z, Y. These annular elements 41*a*, 41*b* are joined together by a central connection element 41*c* in order to form a single piece.

In order to control the movements of the simple cardan joint 40, a first blocking screw 42 to block the rotation around the first axis of rotation Z and a second blocking screw 43 to block the rotation around the second axis of rotation Y are provided.

Both the first and the second blocking screws 42,43 are provided on the head with a shaped impression, preferably hexagon-like, for engaging with a screwing tool.

The proximal rod 2 is connected to the simple cardan joint 40 by means of a distraction/compression device 20.

This distraction/compression device 20 comprises a distraction/compression body 21 having a threaded hole which a distraction/compression pin 22 operated by a ring nut 23 screws into.

A blocking screw 24 of the distraction/compression pin 22 screws into a transversal threaded hole 22*a* of the distraction/compression pin 22 passing through a slot 21*b* that is present on the distraction/compression body 21.

The proximal rod 2 is attached to an end of the distraction/compression pin 22.

The connection between the arched element 5 supporting the distal rod 3 and the distraction/compression device 20 supporting the proximal rod 2 is thus performed by means of the simple cardan joint 40.

In particular, an annular element 41*a* of the simple cardan joint 40 is connected to the support element 6 by means of the first blocking screw 42 acting as a pin of rotation around the axis Z. In the example, the annular element 41*a* is interposed between a pair of rings 6*a* that are present on the support element 6.

While the other annular element 41*b* of the simple cardan joint 40 is connected to the distraction/compression body 21 by means of the second blocking screw 43 acting as a pin of rotation around the axis Y. In the example, the annular element 41*b* is interposed between a pair of rings 21*a* that are present on the distraction/compression body 21.

In the example, the support element 6 has a fork-like shape having two opposing arms which the arched element 5 rotates in.

When the two proximal and distal rods are substantially aligned along a common line, the arc subtended between this common line and the line developing along the longitudinal extension of the fork arms is equal to about 45°. Due to this particular arrangement, the overall dimensions of the articulated device 1 are extremely reduced.

In the example shown, the pin 52 passes through two opposing holes that are present at one end of the arms of the support element 6, while the insert 53 passes through two opposing holes that are present at the other end of the arms of the support element 6. These last two holes have the central axis that is perpendicular to the central axis of the pair of rings 6*a* which the first blocking screw 42 passes through and parallel to the axis X of the pin 52.

Preferably, the arched element 5 is made of a radio-transparent material, such as for example peek reinforced with carbon fibers; the pin 52 is made of steel and the support element 6 of aluminum alloy, but with a thickness not preventing x-ray transparency in order to see the fracture site.

The support element 6, in correspondence with the end which the pin 52 passes through has a circular element 6*b* whose center is in line with the axis of rotation X.

In practice, the pin 52, that is channeled to allow the Kirchner wire to pass through, and the circular element 6*b* have the same central axis, corresponding to the axis of rotation X of the arched element 5.

In this way, when centering the device 1 by means of an X-ray inspection in scopy (continuous exposition to soft x rays), the operator is helped in centering due to the fact that he observes the circular element 6*b* (sub-transparent) and the pin 52 (completely opaque) centered on the same axis.

The circular element 6*b* has a higher radius than that of the pin 52, therefore, when they are in line, a small circle represented by the pin 52 within the greater circle represented by the circular element 6*b* can be observed in scopy.

As it can be appreciated from the above, the device according to the present invention allows the requirements and drawbacks mentioned in the introduction of the present description with reference to the prior art to be met and overcome.

Of course, a person skilled in the art can apply numerous modifications and variants to the above-described above, in order to satisfy contingent and specific requirements, all of which are covered by the scope of protection of the invention, as defined by the following claims.

The invention claimed is:

1. Articulated device for the wrist, comprising:
   a proximal connector for housing a proximal attachment system for pins;
   a distal connector for housing a distal attachment system for pins;

an articulator joint to provide a controlled movement between the proximal connector and the distal connector, said articulator joint comprising an arched element that is directly hinged on a support element about an axis of rotation corresponding to the axis of rotation by flexion and extension of the wrist, said axis of rotation offset from a common line formed when the proximal connector and distal connector are substantially aligned, said arched element being connected to the distal connector, the articulator joint further comprising blocking means to block the rotation of the arched element and rotation-limiting means to limit the rotation of the arched element for a pre-established portion of a circumferential arc, wherein said arched element is directly connected to the distal connector, and in that both the blocking means and the rotation-limiting means are directly mounted on said support element, and in that said support element is mounted by means of a simple cardan joint on the proximal connector, said simple cardan joint presenting a first axis of rotation that is perpendicular to the axis of rotation of the arched element, and a second axis of rotation that is perpendicular to the first axis of rotation and movable with respect to the axis of rotation of the arched element along a circumferential arc whose center is located on the first axis of rotation.

2. Articulated device according to claim 1, wherein said arched element is hinged onto a pin that has a hole in its center to allow a Kirschner wire to pass through for the centering of the articulation axis.

3. Articulated device according to claim 2, wherein said support element presents a circular element whose center is in line with the axis of rotation of the arched element and which is located next to the pin, said circular element being made of a partially x-ray permeable material and said pin being made of an x-ray impermeable material.

4. Articulated device according to claim 1, wherein said blocking means comprise a locking grub screw that can be operated in rotation from the outside, whose end is intended to abut against an edge of the arched element.

5. Articulated device according to claim 4, wherein said limiting means comprise an axially displaceable insert, said insert being provided with a threaded channel which said locking grub screw passes through.

6. Articulated device according to claim 5, wherein said insert comprises an eccentric body that is intended to abut against a ribbed profile that is present on the perimeter of a portion of said arched element.

7. Articulated device according to claim 1, wherein said single cardan joint comprises a connecting element formed by a pair of annular elements having their respective central axis corresponding to said first and second axis of rotation, said annular elements being joined together by a central connection element so as to form a single piece.

8. Articulated device according to claim 1, wherein said simple cardan joint comprises a first blocking screw to block the rotation around said first axis of rotation and a second blocking screw to block the rotation around said second axis of rotation.

9. Articulated device according to claim 1, wherein said proximal connector is connected to the simple cardan joint by means of a distraction/compression device.

10. Articulated device according to claim 8, wherein said distraction/compression device comprises a distraction/compression body that is rotatably connected to its end with respect to said second axis of rotation, said distraction/compression body presenting a threaded hole to receive a distraction/compression pin operated by a ring nut.

11. Articulated device according to claim 10, comprising a blocking screw of the distraction/compression pin that screws into a transversal threaded hole of the distraction/compression pin, passing through a slot on the distraction/compression body.

12. Articulated device for the wrist, comprising:
a proximal connector for housing a proximal attachment system for pins;
a distal connector for housing a distal attachment system for pins;
an articulator joint to provide a controlled movement between the proximal connector and the distal connector, said articulator joint comprising an arched element that is directly hinged on a support element about an axis of rotation corresponding to the axis of rotation by flexion and extension of the wrist, said arched element comprising a concave cylindrical surface having an arc shaped directrix, said directrix lying on a plane that is perpendicular to the axis of rotation of the arched element, said arched element being connected to the distal connector, the articulator joint further comprising blocking means to block the rotation of the arched element and rotation-limiting means to limit the rotation of the arched element for a pre-established portion of a circumferential arc, wherein said arched element is directly connected to the distal connector, and in that both the blocking means and the rotation-limiting means are directly mounted on said support element, and in that said support element is mounted by means of a simple cardan joint on the proximal connector, said simple cardan joint presenting a first axis of rotation that is perpendicular to the axis of rotation of the arched element, and a second axis of rotation that is perpendicular to the first axis of rotation and movable with respect to the axis of rotation of the arched element along a circumferential arc whose center is located on the first axis of rotation.

* * * * *